(12) United States Patent
Belcher et al.

(10) Patent No.: US 9,031,188 B2
(45) Date of Patent: May 12, 2015

(54) INTERNAL IMAGING SYSTEM

(71) Applicant: Georgetown Rail Equipment Company, Georgetown, TX (US)

(72) Inventors: Jeb Belcher, Austin, TX (US); Charles Wayne Aaron, Salado, TX (US)

(73) Assignee: Georgetown Rail Equipment Company, Georgetown, TX (US)

( * ) Notice: Subject to any disclaimer, the term of this patent is extended or adjusted under 35 U.S.C. 154(b) by 225 days.

(21) Appl. No.: 13/762,052

(22) Filed: Feb. 7, 2013

(65) Prior Publication Data
US 2013/0202090 A1    Aug. 8, 2013

Related U.S. Application Data

(60) Provisional application No. 61/596,552, filed on Feb. 8, 2012.

(51) Int. Cl.
| | |
|---|---|
| *G01N 23/02* | (2006.01) |
| *G01N 23/203* | (2006.01) |
| *G01N 9/36* | (2006.01) |
| *G01N 9/24* | (2006.01) |

(52) U.S. Cl.
CPC .............. *G01N 23/203* (2013.01); *G01N 9/36* (2013.01); *G01N 9/24* (2013.01)

(58) Field of Classification Search
CPC ..... G01N 23/04; G01N 23/18; G01N 23/203; G01N 23/20
USPC .................................... 378/58, 86, 89, 87, 88
See application file for complete search history.

(56) References Cited

U.S. PATENT DOCUMENTS

| | | | |
|---|---|---|---|
| 4,468,966 A | 9/1984 | Bradshaw | |
| 5,859,893 A | 1/1999 | Moorman et al. | |
| 7,389,694 B1 * | 6/2008 | Hay et al. ......................... | 73/635 |
| 8,033,724 B2 | 10/2011 | Edwards et al. | |
| 8,094,781 B1 | 1/2012 | Safai et al. | |
| 8,116,529 B2 | 2/2012 | Edwards | |
| 8,542,876 B1 | 9/2013 | Engel et al. | |
| 2009/0110147 A1 | 4/2009 | Safai et al. | |
| 2009/0128557 A1 | 5/2009 | Finlayson et al. | |
| 2009/0132179 A1 * | 5/2009 | Fu et al. ........................ | 702/34 |
| 2010/0223163 A1 | 9/2010 | Edwards | |
| 2010/0327174 A1 | 12/2010 | Edwards et al. | |
| 2013/0255385 A1 | 10/2013 | Edwards et al. | |
| 2013/0260016 A1 | 10/2013 | Georgeson et al. | |
| 2013/0279645 A1 | 10/2013 | Liesenfelt et al. | |
| 2013/0287169 A1 | 10/2013 | Liesenfelt et al. | |
| 2013/0297633 A1 | 11/2013 | Edwards et al. | |

OTHER PUBLICATIONS

International Search Report & Written Opinion dated Apr. 19, 2013 issued in PCT/US13/25374.

* cited by examiner

*Primary Examiner* — Courtney Thomas
(74) *Attorney, Agent, or Firm* — Parsons Behle & Latimer

(57) ABSTRACT

A system for the inspection of the internal structure of a target includes at least one x-ray source that emits collimated x-rays to irradiate the target. At least one detector is positioned to detect backscatter x-rays from the target. The detector may include a collimation slot that limits the field of view of the detector. The target may be a railway component and the system may inspect the internal structure of the component as it is moved along the railway by a vehicle. The system may detect a change in the density of a target based on a comparison of the detected backscatter x-rays. The use of a plurality of segmented backscatter x-ray detectors having a collimation slot may pixelate the internal image in the direction of the collimation slot.

32 Claims, 14 Drawing Sheets

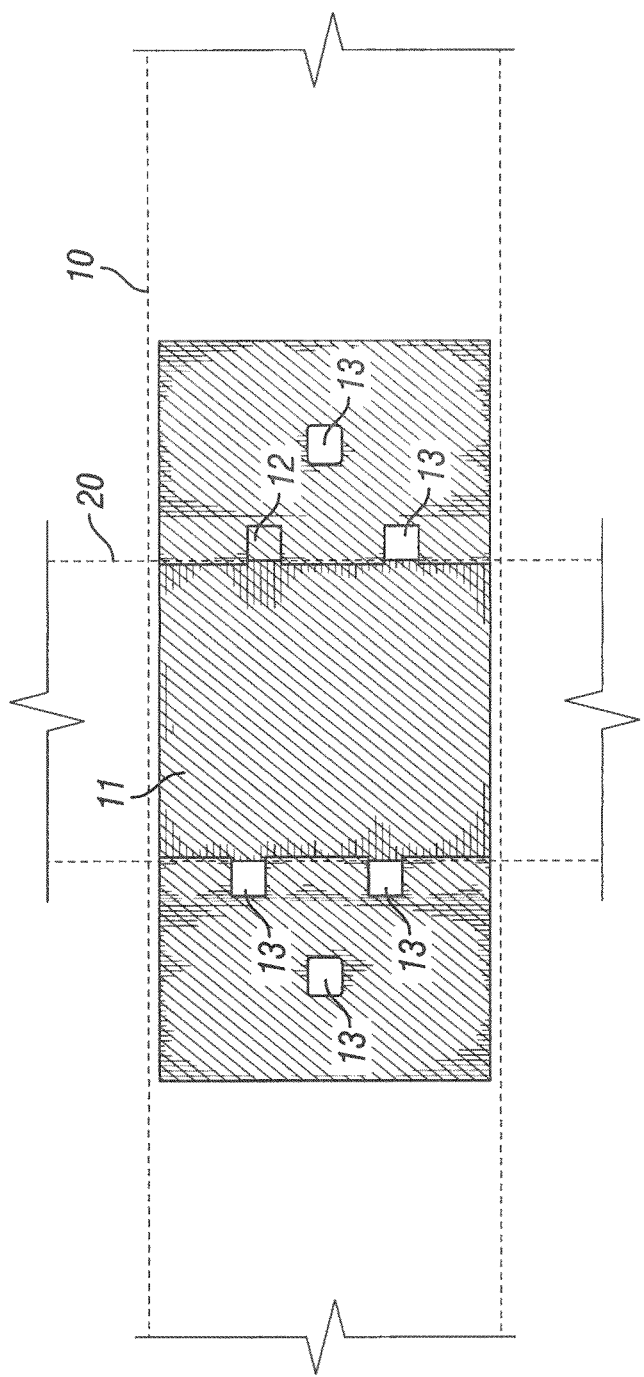

INTERNAL IMAGING SYSTEM

RELATED APPLICATIONS

The present application claims the benefit of U.S. Provisional Patent Application Ser. No. 61/596,552, filed on Feb. 8, 2012 and entitled INTERNAL IMAGING OF RAILWAY COMPONENTS, the disclosure of which is incorporated herein by reference in its entirety.

BACKGROUND

1. Field of the Disclosure

The embodiments described herein relate to an internal imaging system using the detection of backscatter x-rays and may be used for the internal inspection of railway track components.

2. Description of the Related Art

Currently the detection of many internal flaws of railway track components may be found through either destructive or direct-contact methods. Destructive inspection methods may not be desired as the component, or at least a portion of the component, is damaged and/or destroyed. Direct-contact methods of inspection are typically slow, reducing the amount of track that may be inspected during a single date to detect potential flaws in the railway track components. For these reasons and in order to increase track component inspection productivity, reliability, and accuracy there is a great need for improved automated inspection methods.

Some flaws may currently be detected using a destructive inspection method. For example, a hollow region in a tie can be exposed through a destructive method such as cutting a cross-section with a chain saw. Such a defect is important to find because if a hollow or decayed region of a tie is in the spike area it may comprise the spike holding ability of the tie as well as the load bearing capacity of the tie.

One conventional non-destructive inspection technique is to "ping" the tie by throwing a rock at it, kicking the tie itself, and/or striking it with an object. An inspector tries to determine whether the tie is hollow or not based on the sound created by striking the tie. This assessment is subjective in nature and requires a human tie-by-tie evaluation. Further, the portion of the tie having a void or decayed region may not be struck by the random kicking or hitting of the tie. This method of determining faulty ties may not be highly accurate in determining whether a tie is faulty.

It has been estimated according to one American Railway Engineering Association study that 44% of wood tie failures are due to decay and deterioration that may not be visible from the surface. Other failure modes are estimated at 18-20% plate cutting, 16-18% splitting, 14-16% spike kill, and the remaining by a broad range of additional reasons (termite infestation, etc.). A true objective inspection system would be able to collect both surface and internal images, with the ability to forecast a tie's remaining life accordingly.

There are other examples of railway track component flaws that illustrate the need for an Internal Imaging solution. For example, one flaw is a crack in a concrete tie. Often a crack in a concrete tie may be positioned under the ballast level and thus, a track inspector could easily fail to detect this flaw. Taking the time to remove the ballast, inspect each tie at the sub-ballast level, and then replace the ballast takes far too much maintenance time on a rail line.

Another potential flaw that may be detected by an internal imaging system is Rail Base Corrosion (RBC). Although RBC can be found on any track, it is most prevalent in tunnels and/or where the track is electrified. This may be due to the combination of standing water and electricity flowing through the rail acting to rust and erode the rail-base at an increased rate.

The present disclosure is directed to detecting the above identified problems in railway components with non-destructive means. Other than wood ties, concrete ties, and RBC, it would also be beneficial to detect flaws in fasteners, pads, spikes, plates, composite ties, slab track, bridges, and tunnels.

SUMMARY

The present disclosure is directed to an internal imaging system using backscatter x-ray detection and method that overcomes some of the problems and disadvantages discussed above.

One embodiment is an internal imaging system to inspect a plurality of targets along a predetermined path comprising a vehicle configured to travel along the predetermined path and a first x-rays source and a first detector connected to the vehicle. The first x-ray source is configured to irradiate the plurality of targets with a fan beam of x-rays and the first detector is configured to detect backscatter x-rays from the plurality of targets. The predetermined path may be a railway track. The plurality of targets may comprise railway track components.

The system may include a second x-ray source and a second detector connected to the vehicle. The first x-ray source may be configured to irradiate at least a first rail of the railway track with a fan beam of x-rays and the second x-ray source may be configured to irradiate at least a second rail of the railway track with a fan beam of x-rays. The second detector may be configured to detect backscatter x-rays from the plurality of targets. The first and second x-ray sources may be positioned to irradiate the plurality of targets with fan beams positioned between the first and second detectors.

The first detector may be a first plurality of segmented detectors and the second detector may be a second plurality of segmented detectors. The first and second detectors may include a collimation slot. The system may include a processor in communication with the first and second detectors. The processor may be configured to determine the density of the plurality of targets from the reception of backscatter x-rays by the first and second detectors. The processor may be configured to generate an internal image of the plurality of targets from the reception of backscatter x-rays by the first and second detectors. The system may include a monitor to display the internal images of the plurality of targets. The system may include a surface scanning system connected to the vehicle. The surface scanning system may include at least one laser source and at least one optical source. The laser source may illuminate a portion of the plurality of targets and the optical device may capture an image of the illuminate portion of the plurality of targets.

One embodiment is a method of using an internal inspection system along a predetermined path to conduct an internal inspection of a plurality of targets. The method comprises moving the internal inspection system along a predetermined path and irradiating the plurality of targets along the predetermined path with x-rays from at least one source of x-rays. The inspection system includes at least one source of x-rays and at least one first detector configured to detect backscatter x-rays. The method includes detecting a portion of backscatter x-rays from the plurality of targets with the at least one first detector and generating data relating to an internal structure of the plurality of targets based on the detection of backscatter x-rays by the at least one first detector. The predetermined path may be a railway track and the plurality of targets may be a railway track components.

The method may include detecting an object in at least one target of the plurality of targets. The object may be a void, a foreign object in a void, a material flaw, or a fastener. The method may include analyzing the generated data to determine a density of at least a portion of at least one target of the plurality of targets. The generated data may be an image of an internal structure of at least one target of the plurality of targets. The method may include scanning the plurality of targets with a surface scan, generating a surface image of at least one target of the plurality of targets from the surface scan, and comparing the surface image and the internal image of the at least one target.

The method may include irradiating the plurality of targets with a fan beam or a pencil beam of x-rays. The method may include irradiating the plurality of targets with collimated x-rays. The method may include position the at least one first detector in front of the at least one source of x-rays and positioning at least one second detector being the source of x-rays. The at least one first detector may be a first plurality of segmented detectors and the at least one second detector may be a second plurality of segmented detectors. The method may include analyzing the generated data to identify at least one internal feature of at least one target of the plurality of targets.

One embodiment may be an inspection system comprising a vehicle, a source of collimated x-rays connected to the vehicle, and a detector connected to the vehicle. The source of collimated x-rays is configured to irradiate a plurality of targets positioned along a predetermined path of travel of the vehicle and the detector is positioned to detect backscatter x-rays from the plurality of targets irradiated from the source of collimated x-rays. The detector is configured to generate data upon detection of backscatter x-rays.

The source of collimated x-rays may emit a pencil beam or a fan beam of x-rays. The system may include a processor configured to determine a density or a cross-section of at least one of the plurality of targets based on the data from the detector. The system may include a surface scan system connected to the vehicle. The surface scan system may be configured to generate images of at least a portion of the plurality of targets. The surface scan system may include at least one laser source and at least one optical device. The at least one laser source may illuminate at least a portion of the plurality of targets and the at least one optical device may capture images of the illuminated portion of the plurality of targets. The system may include a processor configured to correlate the data from the detector with the images form the surface scan system. The system may include a processor configured to process the data from the detector to generate internal images of at least a portion of the plurality of targets and to compare the internal images and the images from the surface scan. The system may include a monitor connected to the processor to display internal and captured images.

BRIEF DESCRIPTION OF THE DRAWINGS

FIG. 19 shows a horizontal cross-section of a tie plate connected to a tie generated from an internal inspection system.

Figure 1:
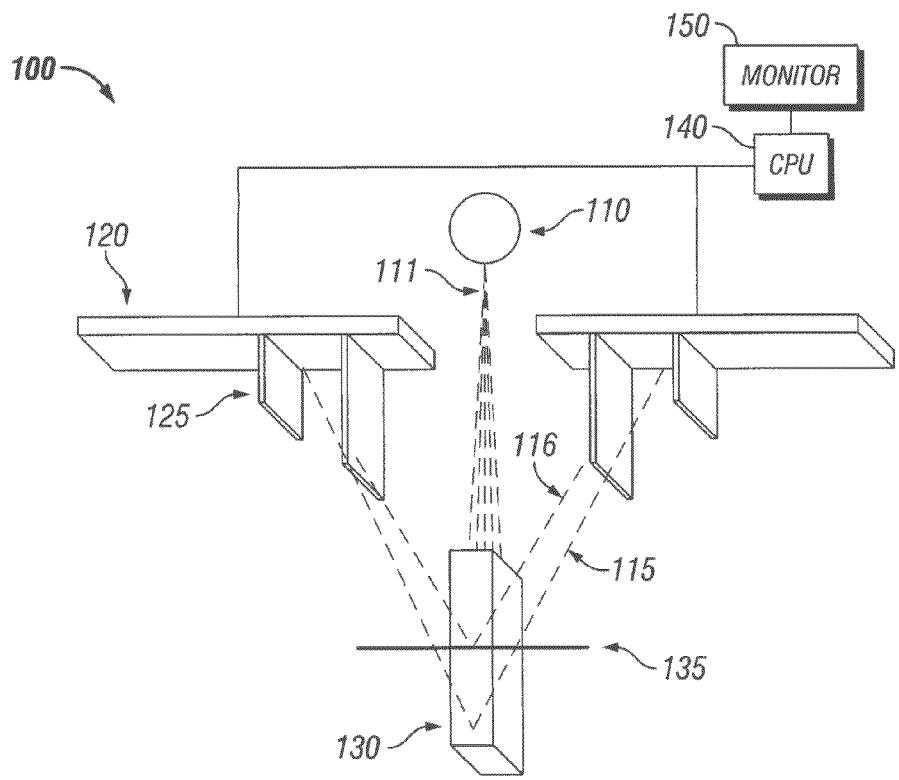
FIG. 1 is a schematic of one embodiment of a backscatter x-ray system using collimation fins.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the scope of the invention as defined by the appended claims.

DETAILED DESCRIPTION

The present disclosure is directed to an internal inspection system that uses backscatter x-ray technology. The internal inspection system may be used alone or synchronized with a video scan or 3D camera scan to provide a surface scan super-imposed on the internal image. One such surface scan is the Aurora system from Georgetown Rail Equipment Company of Georgetown, Tex., as disclosed in U.S. Pat. No. 7,616,329 entitled System and Method for Inspecting Railroad Track, which is herein incorporated by reference in its entirety. The x-ray inspection and video or 3D camera scan may be synchronized by the use of a wheel encoder and/or GPS system. The video scan may provide color images or grayscale images. Alternatively, a comparison of a backscatter x-ray scan and a surface scan may be used to analyze railway components instead of super-imposing the surface scan onto the backscatter x-ray scan. For example, a side-by-side comparison of two scans may be used.

The present disclosure is directed to using backscatter x-ray technology to inspect, for example, the composition of composite materials and material density. Backscatter x-ray technology may also be used to determine the length, height, width, and/or volume of cracks, voids, or other internal flaws. Additionally, the backscatter x-ray technology may be used to determine other aspects of railway components. For example, backscatter x-ray technology may be used to determine if spikes are seated in hollow regions and/or determine if reinforcing structures show signs of fatigue or decomposition. Backscatter x-ray technology may also be used to show material decomposition and/or calculate structural support of an object. Backscatter x-ray technology may be used to inspect joint bars, spikes, plates, ties, rails, rail seat pads, insulators, joint bars, special track work like turnouts or diamonds, and/or fasteners. Backscatter x-ray technology may be used to inspect ballast and potentially to identify low levels of ballast and/or fouled ballast. The disclosed use of backscatter x-ray technology may be used to identify and/or analyze additional railway component features as would be recognized by one of ordinary skill in the art having the benefit of this disclosure.

The detectors may be positioned at any distance from the target that is more than a minimum distance from the top of a rail of a railway. The minimum distance may be about 2.75 inches. The minimum distance may be substantially zero if the internal inspection system is static and the target is moved relative to the inspection system, if necessary. The internal inspection system may be configured to scan railroad components at speeds 10 mph or greater. The system may be configured to permit an increase or decrease in speed during the scan. For example, the speed may be decreased to improve resolution of a particular component, if desired. The inspection system may be used to inspect the internal structure of a target or plurality of targets with no minimum or maximum speed required. The inspection system may also be used to inspect the internal structure of a target or plurality of targets without any movement of the inspection system relative to the target.

The x-ray source for the internal inspection system may be an 1800 Watt x-ray system (450 kV, 4 mA). In one embodiment, the inspection system may use a 450kV, 1 mA x-ray source. The total system power consumption of the entire system may be less than 5400 watts. The total power of the inspection system may be adjusted dynamically to increase or decrease exposure as needed by the target and/or safety requirements. In order to provide power for the backscatter x-ray system, the scanning vehicle may be equipped with a separate generator. More than one scanning unit may be used on the scanning platform requiring additional power.

FIG. 1 is a schematic diagram of an internal inspection system 100 that includes at least one source 110 of collimated or substantially linear x-rays 111. The use of collimated or substantially linear x-rays 111 may permit the internal inspection of a plurality of targets located along a predetermined path as the internal inspection system 100 travels along the predetermined path. The source 110 of collimated x-rays 111 is positioned to irradiate at least one target 130 with collimated x-rays 111. The target 130 may be various items for which it would be beneficial to determine the internal structure and identify any potential flaws within the internal structure of the target 130. For example, the target 130 may be various track components of a railway bed such as, but not limited to, wooden ties, concrete ties, composite ties, rails, fasteners, pads, spikes, plates, and/or slab track. The source 110 of collimated x-rays 111 may irradiate multiple targets at one time using a fan beam, as discussed below, and may be moved along a path of travel to inspect, analyze, and/or display the internal structures of a plurality of targets along the path of travel as would be appreciated by one of ordinary skill in the art having the benefit of this disclosure.

Backscatter x-rays 115 and 116 rebound or bounce from the target 130 and are detected by backscatter detectors 120. Collimation fins 125 may be mounted to a bottom surface of the backscatter detectors 120 to prevent the detection of backscatter x-rays 116 from above a collimation plane 135 within the target 130. The collimation plane 135 is a predetermined standoff distance from the detectors 120 to the area of interest within the target 130. The collimation fins 125 are configured to permit the detection of collimation rays 115 from the target 130 from below the collimation plane 135. The configuration of the collimation fins 125 may be varied to raise or lower the collimation plane 135 within the target 130, as desired.

The internal inspection system 100 may be used to inspect the internal structure of various targets 130, which may be along a predetermined path, including, but not limited to railway track components, transit systems, high speed rail systems, concrete slab track, ballastless track, concrete structures, roadways, tunnels, roofs and/or or any other structure that may present a difficulty positioning a detector 130 on opposite side as the x-ray source 110. The predetermined path may be various pathways as would be appreciated by one of ordinary skill in the art such as a railway, roadway, conveyor belt, and/or manufacturing line. The use of a detector 120 configured to detect x-rays above or below a collimation plane 135 within a target 130 permits the inspection system 100 to only inspect the areas of interest to the party doing the inspection. As discussed above, the detector 120 may include a structure, such as collimation fins, that may be adapted to raise or lower the collimation plane 135 within the target(s) 130.

A computer processing unit (CPU) 140 is in communication with each of the backscatter detectors 120. Data is generated as each of the backscatter detectors 120 detect the backscatter from the target 130. This data may be a pixelated internal image due to the presence of a collimation slot in the detector 120 as discussed below. The CPU 140 receives the data from the backscatter detectors 120 and the CPU 140 may be used to analyze the data to determine potential flaws and/or defects within the target 130. The CPU 140 may store the data from the backscatter detectors 120 for later analysis. The stored data may be inspected by automated computer algorithms or by an inspector. The CPU 140 may be programmed with various algorithms used to analyze the detection data and identify potential flaws and/or defects in the internal structure of the target 130. The algorithms may flag suspect targets or areas of a target(s) to be viewed and/or analyzed by a person. The CPU 140 may be wired or wirelessly connected to the backscatter detectors 120. Further, multiple CPUs 140 may be used to store and/or analyze data generated by the detectors 120. A display or monitor 150 may be connected to the CPU 140 and an image may be displayed on the monitor 150 based on the data received by the CPU 140. The monitor 150 may display the pixelated internal image of the target(s) for analysis and review by an operator.

Figure 10:
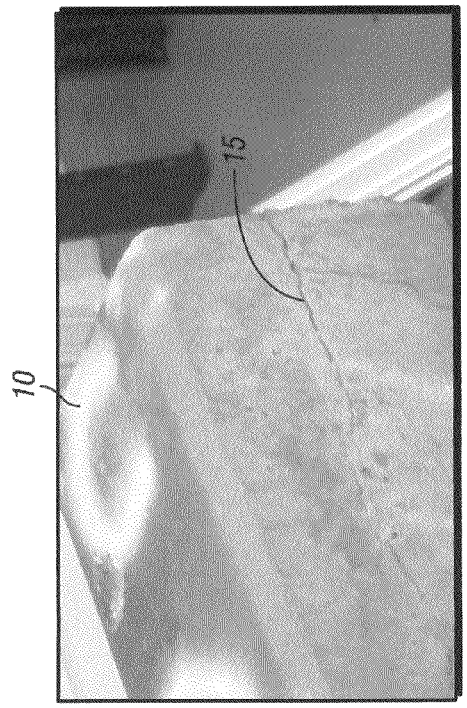
FIG. 10 shows a sub-surface defect in a concrete tie.
Figure 11:
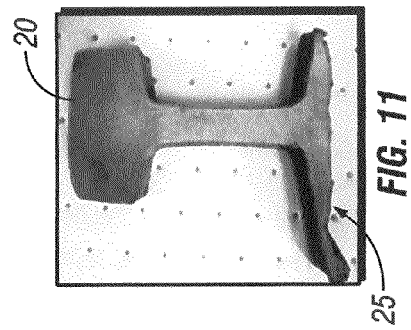
FIG. 11 shows rail seat corrosion on the base of a rail.
Figure 9:
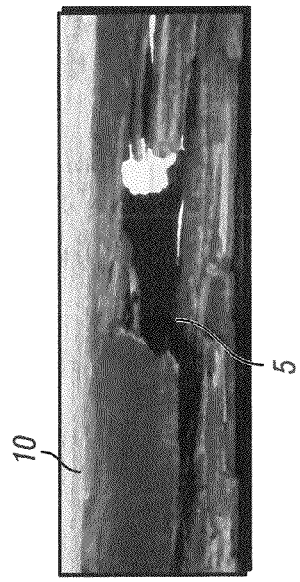
FIG. 9 shows a sub-surface defect in a wooden tie.
Figure 12:
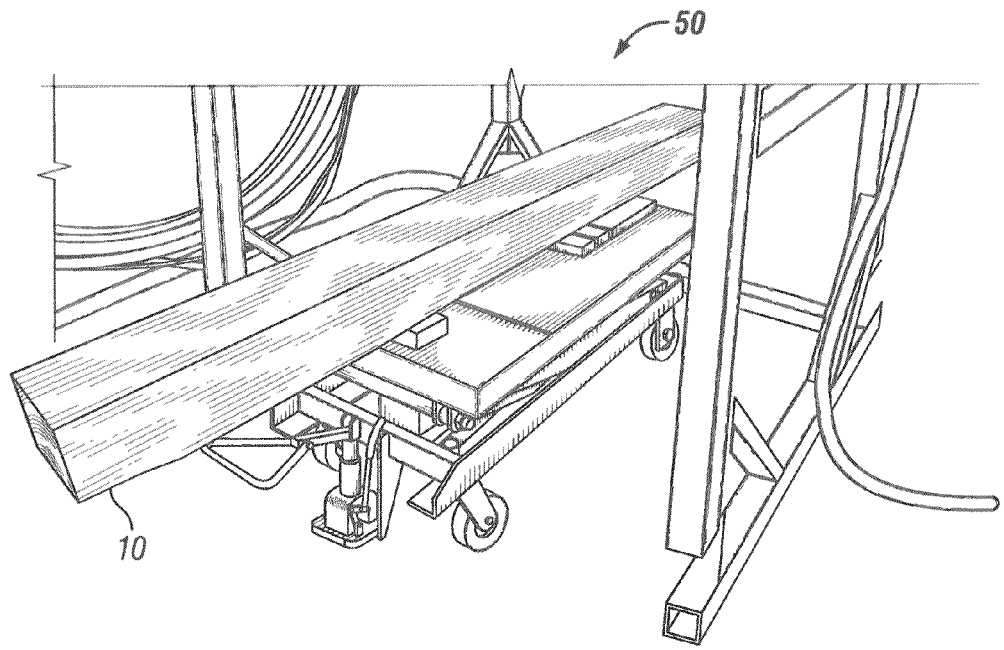
FIG. 12 a manufacturing system that may use a backscatter x-ray inspection system.
Figure 13:
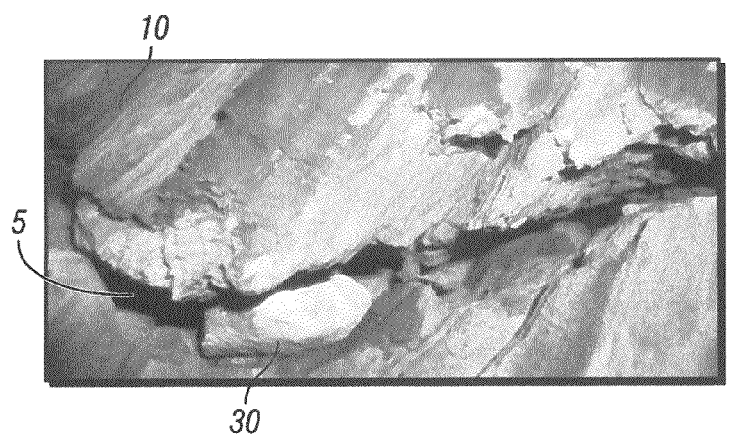
FIG. 13 shows a foreign body positioned within a void in a railroad tie.

The internal inspection system 100 may be used to detect and/or identify various potential flaws within various railroad components. For example, the system 100 may be able to identify a void 5 with a railroad tie 10 as shown in FIG. 9. The system 100 may also be able to identify cracks 15 in a railroad tie 10 as shown in FIG. 10. The system 100 may also be able to detect and/or display RBC 25 on the bottom portion of a rail 20 as shown in FIG. 11. The system 100 may also be able to detect and/or display a foreign object 30 located within a void 5 within a railroad component, such as a tie 10 as shown in FIG. 13. The system 100 also may be beneficial at a manufacturing facility 50 to inspect newly manufactured components, such as a railroad tie 10, for material flaws as shown in FIG. 12. The inspection system 100 may be static with the target, such as a railroad tie 10, moved past the system 100 to inspect the internal structure of the target.

The backscatter detectors 120 of inspection system 100 may or may not include collimation fins 125. The internal structure of a target 130 may be inspected by the inspection system 100 without the creation of an internal image. The backscatter detectors 120 detect backscatter x-rays 115 from a target 130. Multiple portions and/or multiple targets 130 may be inspected and the detection of backscatter x-rays may be compared to determine a change in density in a portion of the target or in an individual target compared to the other targets being inspected. A change in the amount of detected backscatter x-rays by the detector 120 may provide an indication that a portion of target(s) may require further inspection.

Figure 2:
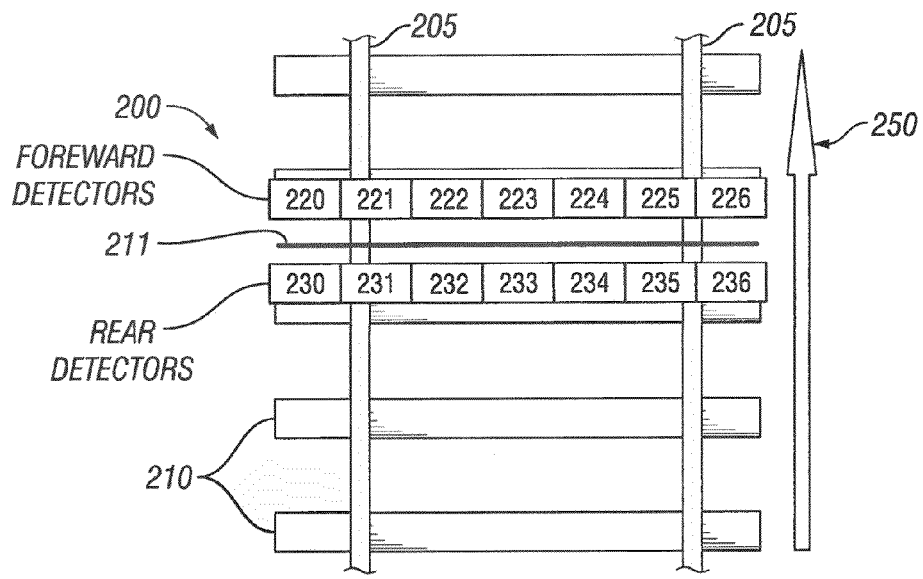
FIG. 2 is a schematic of a backscatter x-ray system used to inspect internal images of railway components.

FIG. 2 shows a schematic diagram of an internal inspection system 200 that may be used to inspect the internal structure of various railway track components, such as rails 205 and ties 210. The system 200 may be attached to a vehicle, such as a locomotive, railcar, or hi-rail vehicle, adapted to travel in a direction 250 along a predetermined path, i.e. the rails 205, to inspect the railway track components. An x-ray source emits an x-ray fan beam 211 along the railway track. The x-ray fan beam 211 may be configured to span and irradiate all of the components of interest. A first bank of segmented detectors 220-226 may be positioned ahead of the fan beam 211, in reference to the direction of travel, and in a parallel orientation to the fan beam 211 to detect backscatter x-rays from the irradiated targets, i.e. components of interest. A second bank of segmented detectors 230-236 may be positioned behind the fan beam 211, in reference to the direction of travel, and in a parallel orientation to the fan beam 211 to detect backscatter x-rays from the irradiated targets, i.e. components of interest. Data from each bank of backscatter detectors 220-226 and 230-236 may be used to analyze the internal structure and/or generate images of the internal structure of the irradiated targets. The number and configuration of segmented detectors 220-226 and 230-236 is for illustrative purposes only. The length and/or number of detectors may be varied as necessary to properly detect backscatter x-rays from the irradiated targets. The segmented detectors may include collimation slots to create a pixelated image based on the backscatter x-rays returned from the target as discussed below.

Figure 3A:
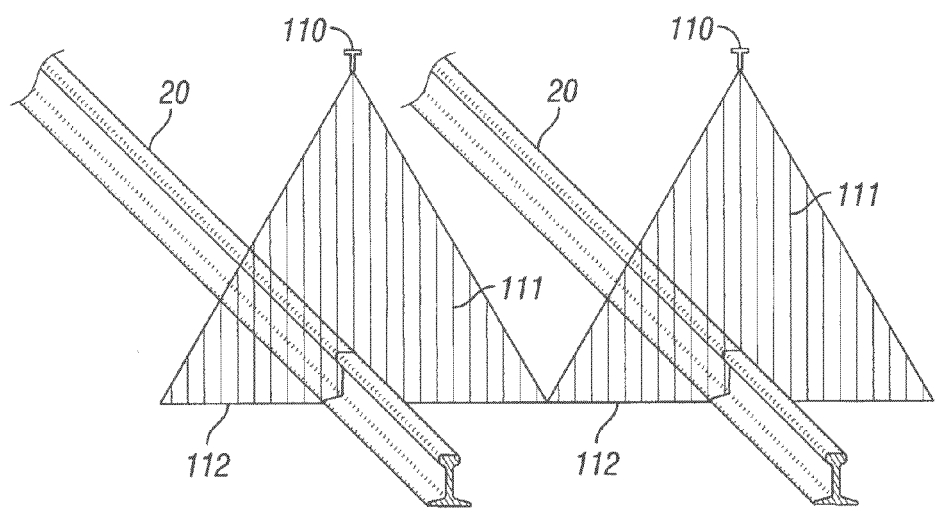
FIG. 3A is a schematic showing two x-ray sources emitting x-rays over two rails of a rail bed.

FIG. 3A shows two sources 110 of collimated x-rays 111 that are used to irradiate the entire cross-section of a railway bed including both rails 20 with a fan beam 112. The location of the two source 110 of collimated x-rays 111 directly above the rails 20 is for illustrative purposes only as the actual configuration may be varied to other locations above the target so as being offset from the rails 20 as would be appreciated by one of ordinary skill in the art having the benefit of this disclosure. The disclosed inspection system may use a single source 110 or two or more sources 110 to properly irradiate the intended target. As discussed above, the speed of the internal inspection system may depend on multiple factors including Quantity of Scanning Units, FOV, and Resolution. The desired speed of scan during the inspection may necessitate the number of sources 110 used by a system to irradiate the intended target. The internal inspection system 100 may also be used as a static system used to inspect the internal structure of a target or targets. The target(s) may be moved past the internal inspection system 100 to inspect the internal structure along the entire length of the target.

Figure 3B:
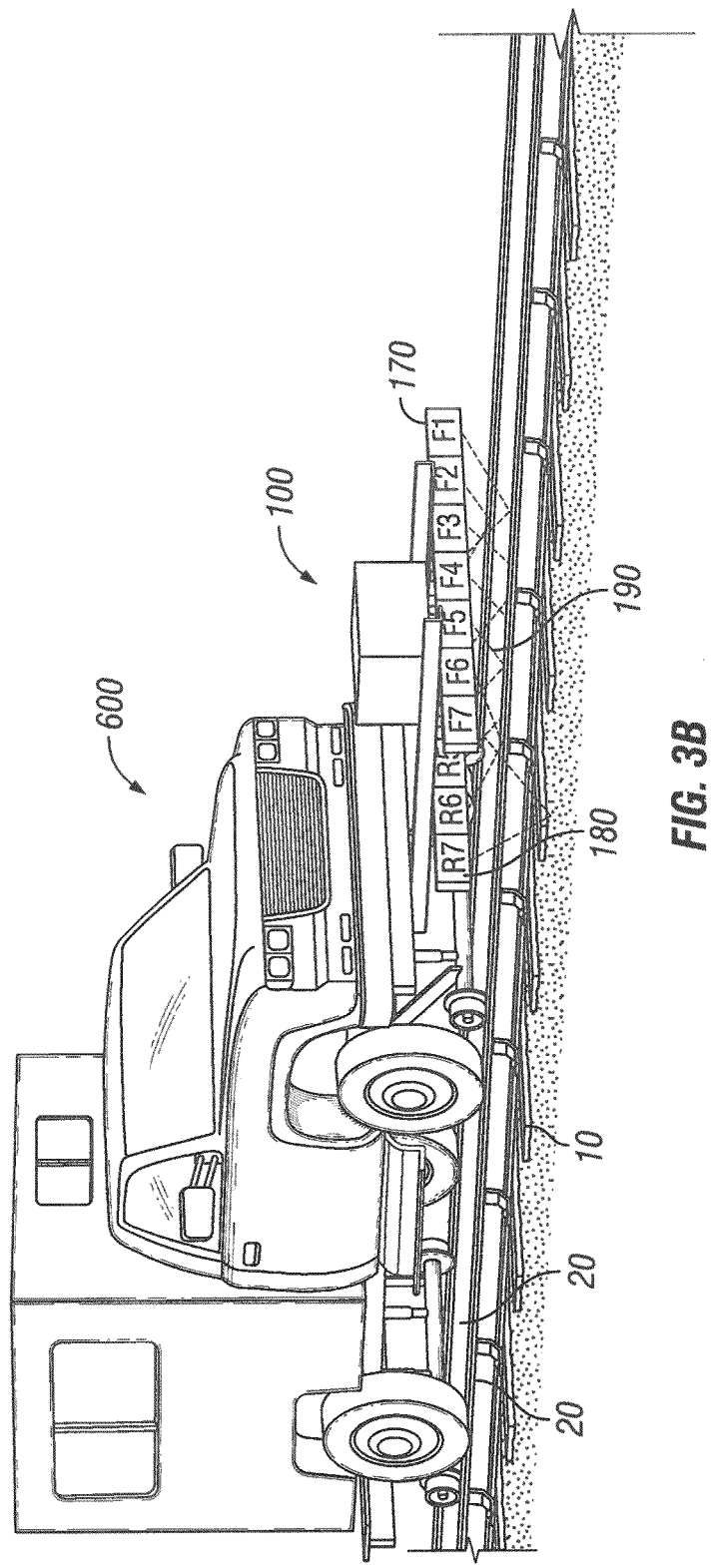
FIG. 3B shows an embodiment of an inspection system connected to a vehicle adapted to travel along the rails of a railway.

FIG. 3B shows an inspection system 100 connected to a vehicle 600 (e.g., a hi-rail truck) adapted to travel along the rails 20 of a railway. The system 100 may include a forward bank 170 of segmented detectors and a rearward back 180 to detect backscatter x-rays 190 from various targets being inspected. The configuration of segmented detectors 170 and 180 and connection to the vehicle 600 is for illustrative purposes only. The vehicle 600 may permit the inspection system 100 to travel along a predetermined path at a relatively high rate of speed to inspect targets along the predetermined path. The speed may be considered as a high rate of speed in regards to convention inspection systems. For example, the vehicle 600 may travel at 5 to 10 miles per hour, or faster, along the predetermined path while the inspection system 100 irradiates and detects backscatter x-ray from a plurality of targets positioned along the predetermined path. The inspection system 100 may be connected in various ways to a vehicle adapted to travel along the railway. For example, the inspection system 100 may be connected to the rear of the vehicle 600 and the vehicle may be various other vehicles such as a locomotive. The number of individual segmented detectors as well as the number and configuration of banks of detectors may be varied as would be appreciated by one of ordinary skill in the art having the benefit of this disclosure.

Figure 4:
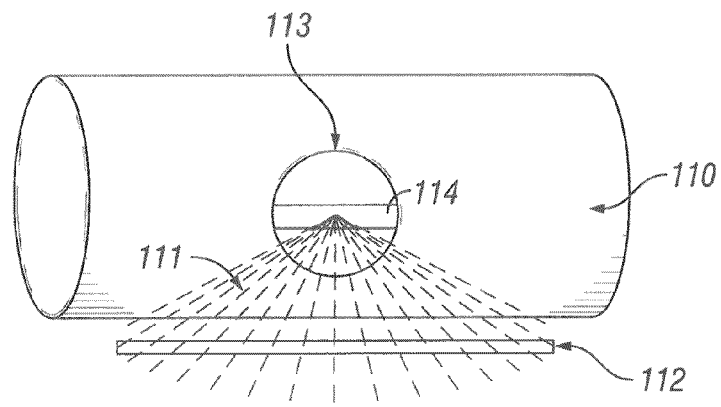
FIG. 4 shows an embodiment of a collimated x-ray source.

FIG. 4 shows an embodiment of a static source 110 of collimated x-rays 111 that may be in the form of a fan beam 112. One potential x-ray source 110 is a MXC-451HP/11 x-ray tube commercially offered by Comet of Stamford, Conn. The source or x-ray tube 110 includes an aperture 113 through which x-rays may be emitted. The aperture 113 is partially covered leaving only a collimation slot 114 through with x-rays may be emitted. The collimation slot 114 collimates the x-rays that are emitted from the source 110. The configuration of the collimation slot 114 may result in a fan beam 112. A collimation slot 114 is a static source of collimating x-rays as opposed a dynamic source of collimation x-rays such as using a curved collimator that rotates. Other types of beams may be emitted from a static collimator such as a pencil beam of x-rays (not shown) depending on the configuration of the collimation slot 114. The source 110 with the collimation slot 114 may be used to irradiate a desired target(s) with collimated x-rays 111.

Various configurations may be used to statically collimate the x-rays from the x-ray source 110 as would be appreciated by one of ordinary skill in the art. For example, the x-ray source may include a collimation slot, a cylindrical aperture, or a cone shaped aperture. The static collimation of the x-rays may permit an inspection system 100 to travel along a predetermined path at a relatively high speed while inspecting a target or a plurality of targets located along the predetermined path. The predetermined path may be a railway and the targets may be railroad components. The static collimation of the x-rays may also permit the movement of a target along a predetermined path with respect to a stationary inspection system 100. For example, a railroad tie may be moved along a predetermined path underneath the inspection system 100 to permit the irradiation of tie along its entire length with the source 110 of the inspection system 100. The detectors 120 may be positioned adjacent to the target(s) to detect the backscatter x-rays from the target(s). The detection of backscatter x-rays may be used to determine the density of the target(s) as well other internal features and/or flaws of the target(s). The detection of backscatter x-rays may be used to create a cross-section of the target(s). FIG. 19 shows a horizontal cross-section generated by the internal inspection system 100 of the plane of a tie plate 11 connected to a tie 10 and a rail 20. The cross-section shows a spike 12 connecting the tie plate 11 to the tie 10 as well as spike holes 13. The cross-section of a target may be used to determine potential internal flaws of the structure of the target. The cross-section of a target may be used in comparison with results from a surface scan to identify potential flaws with a target.

Figure 5:
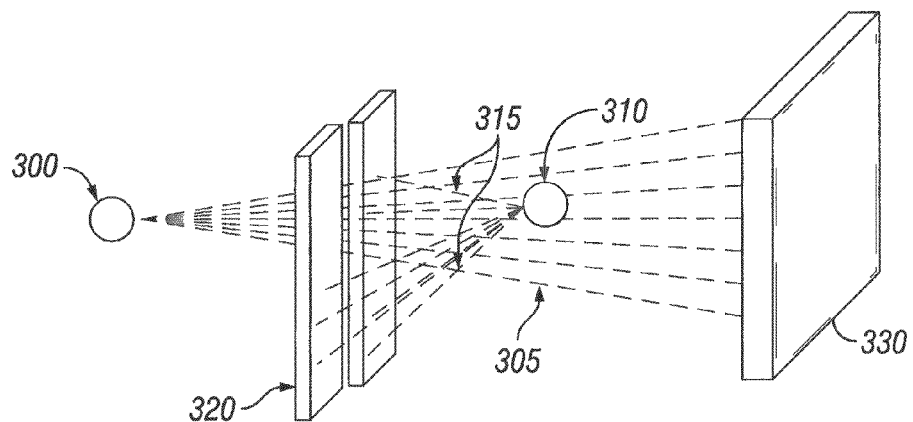
FIG. 5 is a schematic showing backscatter x-ray detectors in comparison to traditional x-ray detectors.

FIG. 5 shows a schematic diagram that compares backscatter x-ray detection with conventional x-ray detection. To scan with traditional x-ray technology, the x-rays 305 are transmitted from a source 300, pass through a target object 310, and are received on the opposite of the target object by a detector 330. As the x-rays 305 pass through the target 310 different portions of the target 310 may affect the rate at which the x-rays pass through the target 310. The x-rays 305 then continue on and irradiate the detector 330. The interaction on the x-rays 305 with the target 310 is used by the detector 330 to generate an image of the internal structure of the target 310.

When inspecting some targets 310, such as railway components, it is not feasible to position a detector opposite of the target from the x-ray source 300 since railway components are typically on the ground. Instead, backscatter x-ray detectors 320 are positioned between the x-ray source 300 and the target 310 and are the backscatter detectors 320 are configured to detect backscatter x-rays 315 from the target 310. The amount and location of the detected backscatter x-rays may be used to determine the internal structure of the target 310. Because the detector 320 picks up the rays that bounce back off of the target 310, this type of detection may require a much lower level of energy than traditional x-ray technology.

Figure 7:
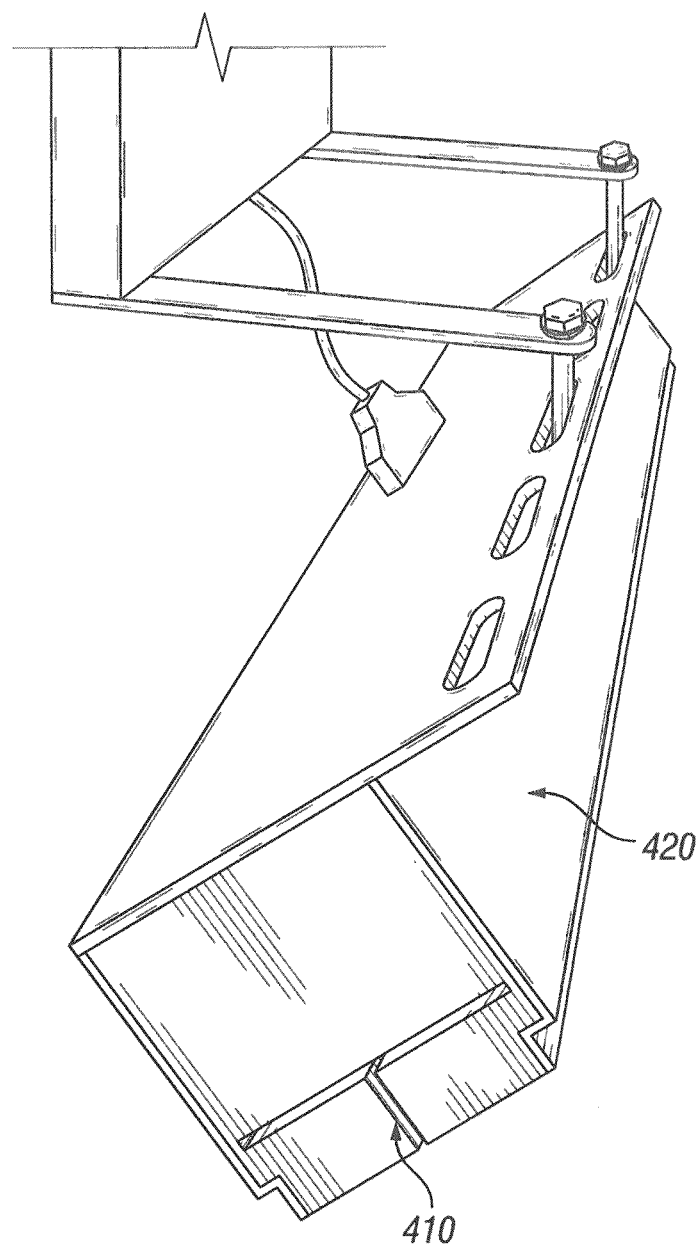
FIG. 7 shows an embodiment of a segmented backscatter x-ray detector with a collimation slot.

FIG. 7 shows one embodiment of a segmented backscatter x-ray detector 420. As discussed above, various numbers of segmented detectors 420 may be used in a bank of detectors to detect backscatter x-rays from an irradiated target. A line scan detector could also be used to detect backscatter x-rays from the targets. One potential detector 420 is a XH8800 Series Line-Scan Camera commercially offered by X-Scan Imaging Corporation of San Jose, Calif. The backscatter x-ray detector 420 may include a collimation slot 410 that limits the field of view of the detector. The detector 420 will only detect the backscatter x-rays that enter through the collimation slot 410. The field of view of the detector 420 is limited by the width and depth of the slot as well as the orientation of the slot to both the target and the x-ray source. The use of a plurality of segmented backscatter x-ray detectors 420 may create a pixelation of the internal image of the target or targets. Each pixel of the internal image is created because the detector is segmented in small regions. The resolution of the internal image along the direction of the slot 410 may be due to the spacing and/or number of segmented detectors 420. The resolution of the internal image in the direction of travel 250 (shown in FIG. 2) may be due to the speed of travel of the inspection system and the sample rate of the segmented detectors 420.

Figure 6A:
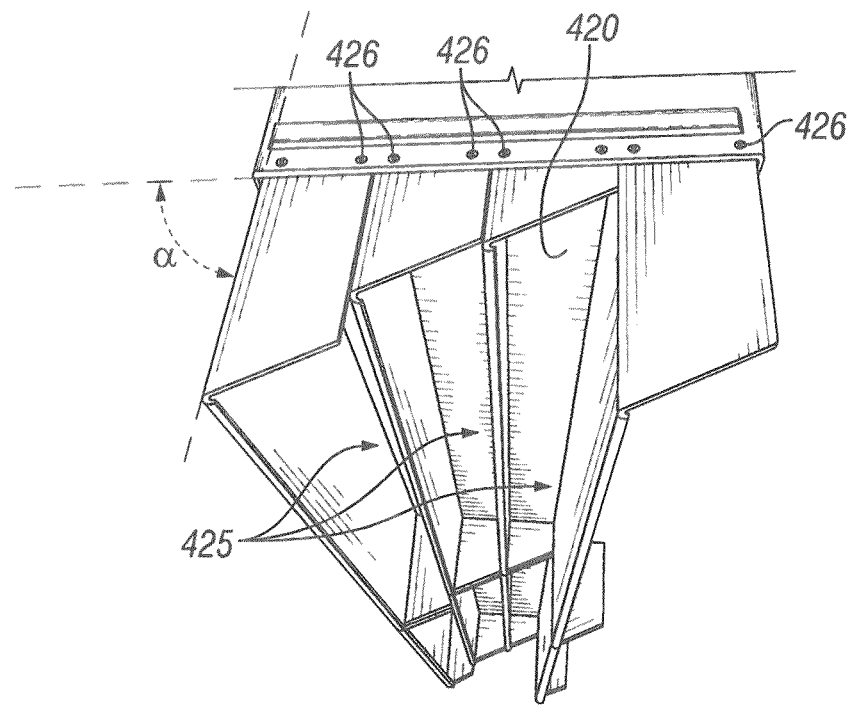
FIG. 6A is one embodiment of a detector with collimation fins.
Figure 6B:
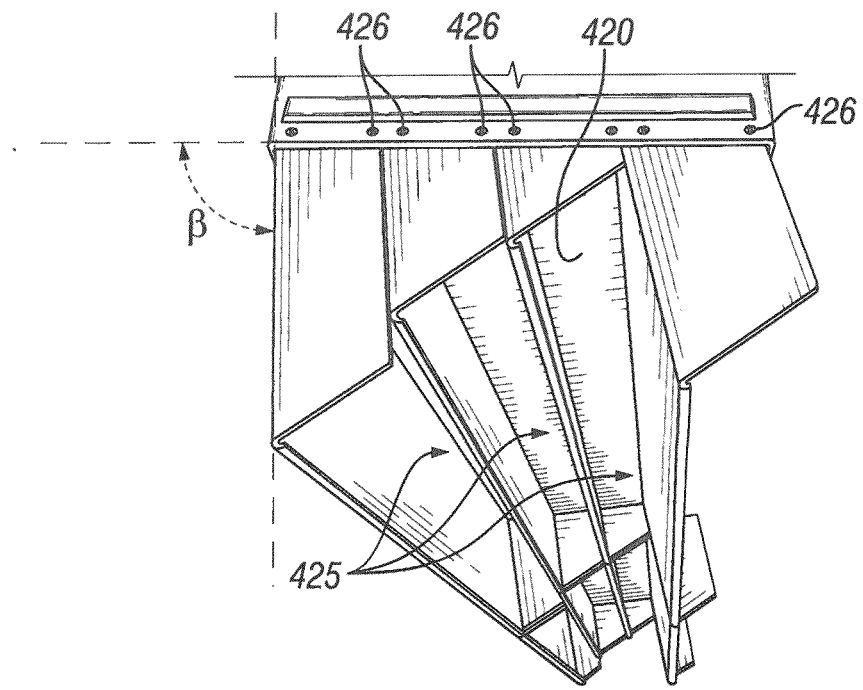
FIG. 6B is the detector of FIG. 6A with the configuration of the collimation fins modified.

FIG. 6A shows a segmented detector 420 that may be used as part of an internal inspection system to detect backscatter x-rays from a target. The segmented detector 420 includes a plurality of collimation fins 425 to block the detection of backscatter x-rays from undesired portions of a target. The collimation fins 425 may also block the detection of backscatter x-rays from structures near or adjacent to the intended target. The collimation fins 425 may be connected by various fasteners 426 that permit the modification of the configuration of collimation fins 425 attached to the bottom of the segmented detector 420. For example, a given fastener may be loosened and the angle of orientation of a single fin 425 or a plurality of the fins 425 may be varied to change the amount and/or angle of backscatter x-rays that the fin(s) 425 prevent from being detected by the detector 425. Additionally, fins 425 may be removed and/or replaced with fins 425 having a different length. The fins 425 may be configured to prevent the detection of any backscatter x-rays that are from above a collimation plane within an intended target, as would be appreciated by one of ordinary skill in the art having the benefit of this disclosure. The collimation fins 425 may be used to prevent the detection from unwanted areas of the target or from objects adjacent a target, such as a rock sitting on top of a railway tie. FIG. 6B shows the segmented detector 420 with the collimation fins 425 in a different configuration to change the collimation plane within the target(s). The configuration of the collimation fins 425 may be varied in various ways. For example, the angle of some or all of the collimation fins 425 may be varied as illustrated by angle β in FIG. 6B in comparison to angle α in FIG. 6A. The configuration of the collimation fins 425 may be altered in other various ways such as removal of some or all of the fins and/or the lengthening of some or all of the collimation fins 425.

Figure 8:
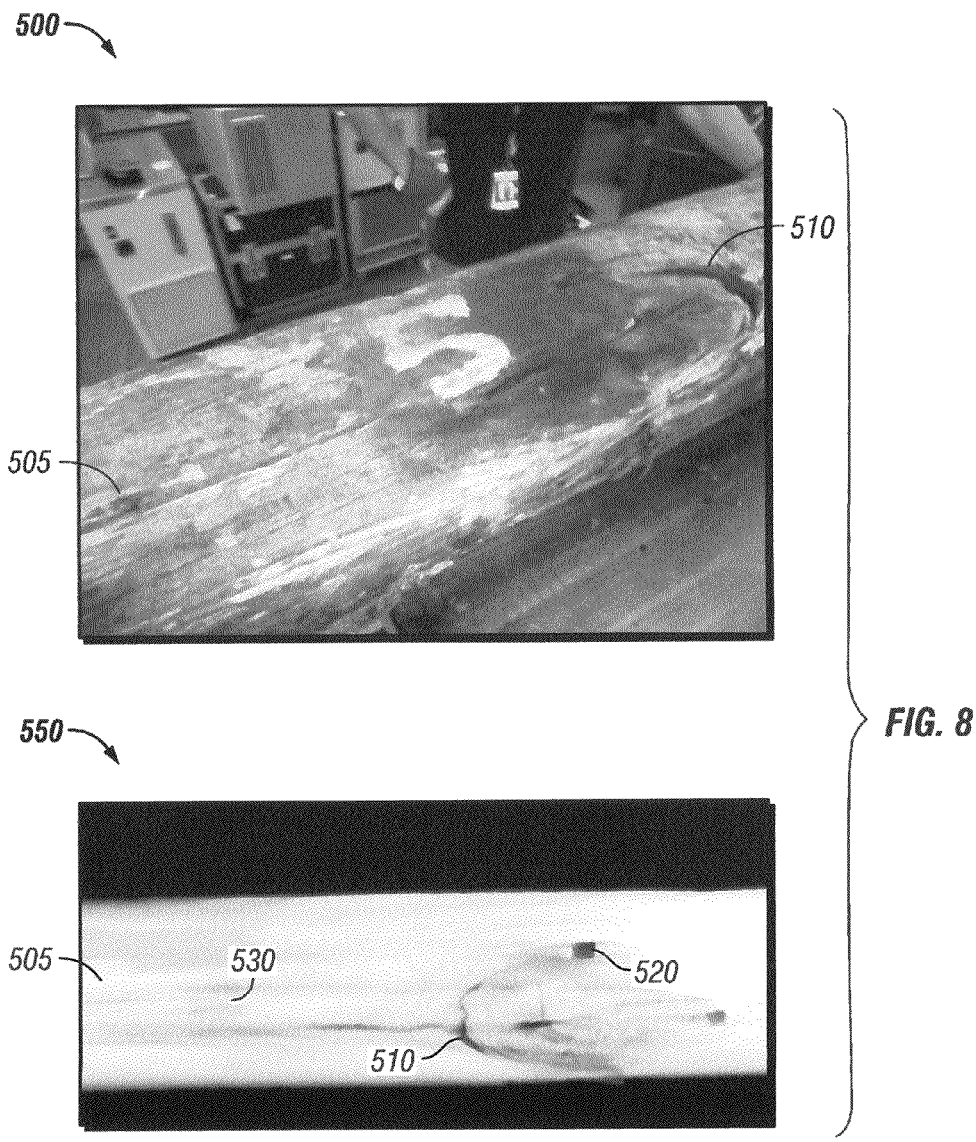
FIG. 8 shows a rail road tie and the pixelated image of the rail road tie.

FIG. 8 shows a picture 500 of a wooden tie 505 that is an intended target of the internal inspection system as well as a gray scale image 550 of the wooden tie 505 generated by the internal inspection system. The gray scale image 550 was created using pixelated image data generated by a segmented backscatter detector having a collimation slot receiving backscatter x-rays as the inspection system passed over the tie 505. The tie 505 includes a surface defect 510 shown in both the picture and the gray scale image as well as various internal structures such as spike hole 520 and a tungsten block 530 shown in the gray scale image 550.

Figure 14:
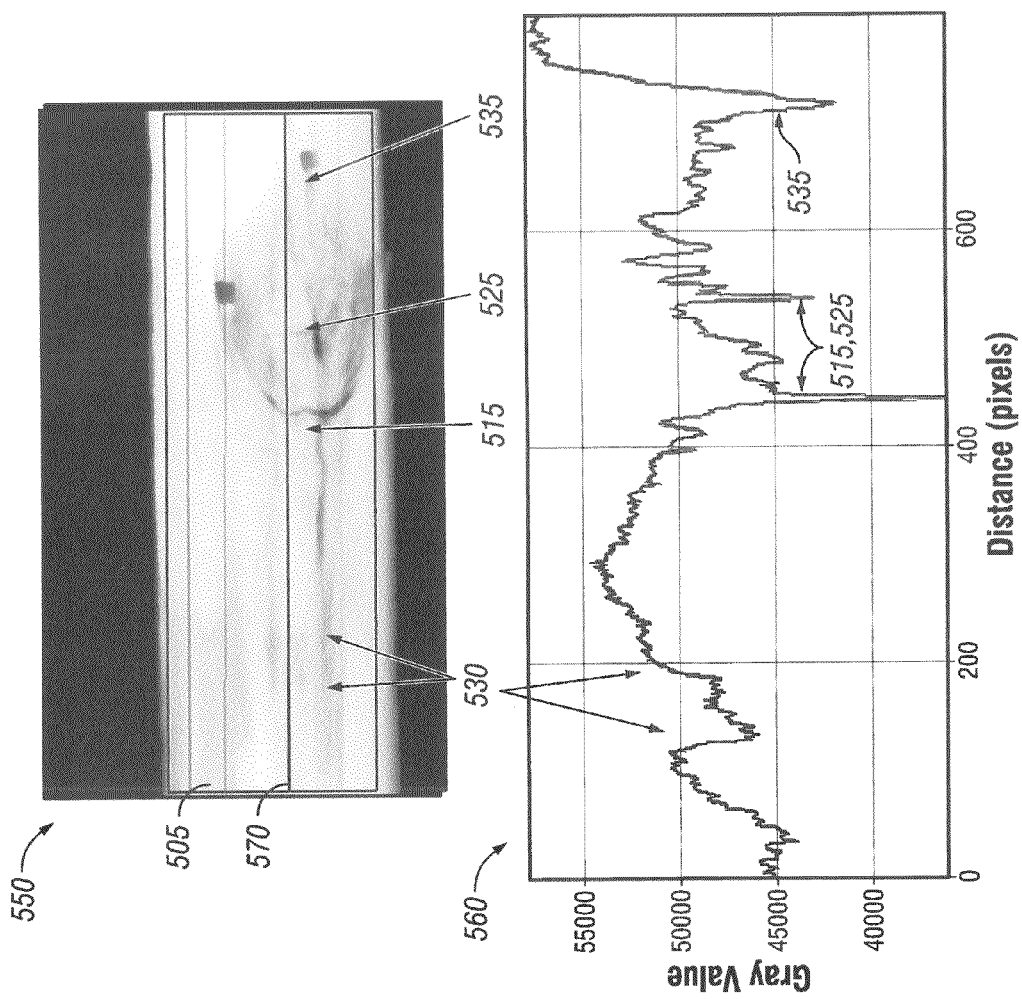
FIG. 14 shows a pixelated image of the rail road tie of FIG. 8 and the raw backscatter x-ray data for a first portion of the railroad tie.
Figure 15:
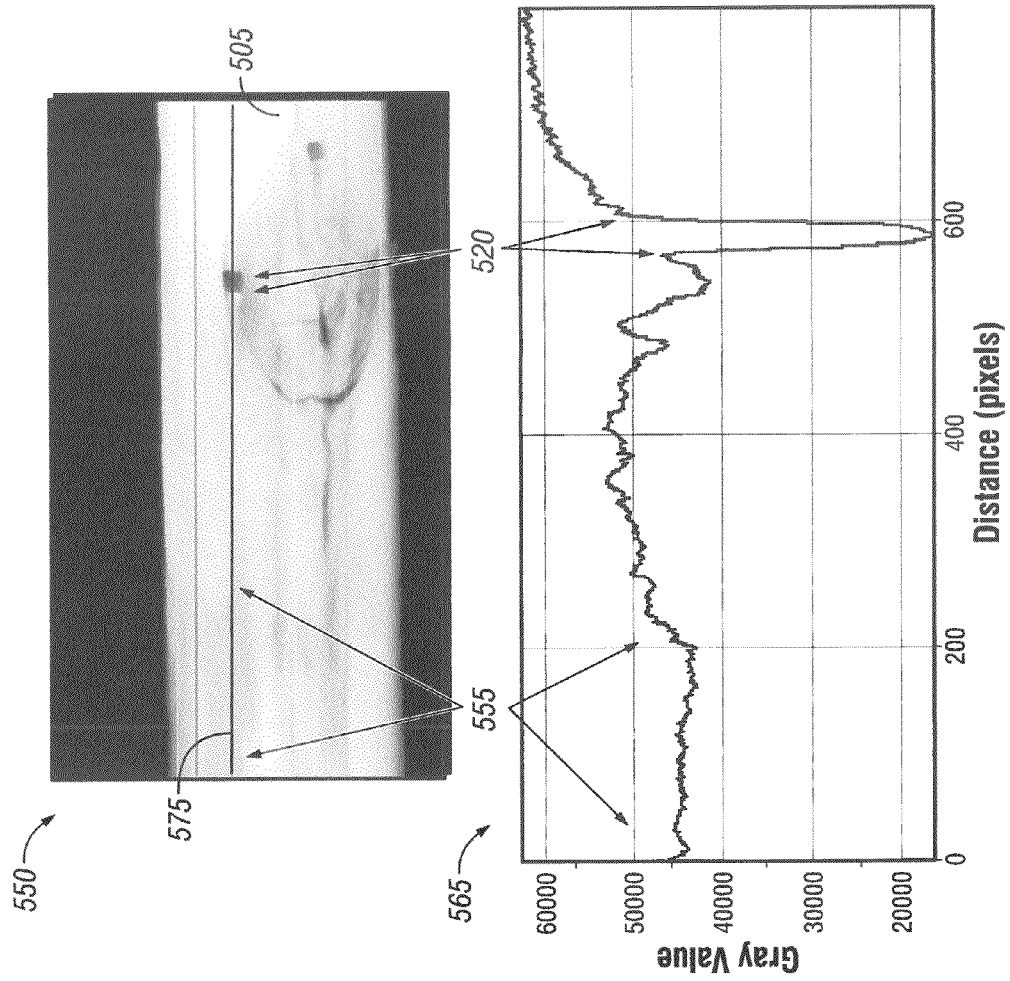
FIG. 15 shows a pixelated image of the rail road tie of FIG. 8 and the raw backscatter x-ray data for a second portion of the rail road tie.

FIG. 14 shows a gray scale image 550 of the wooden tie 505 along with data in the form of a graph 560 that corresponds to a first plane 570 within the wooden tie 505. The gray scale image 550 shows a tungsten block 530 as well as breaks 515, 525, and 535 within the tie 505. FIG. 14 shows the correlation to the images on the gray scale image 550 and the graph 560 of data from a backscatter detector at the first plane 570 in the wooden tie 500. FIG. 15 shows a second plane 575 within the wooden tie 505 on a gray scale image 550. The gray scale image 550 shows a hollow region 555 within the tie 505 as well as a spike hole 520. FIG. 15 shows the correlation of the images on the gray scale image 550 and the graph 565 of data from a backscatter detector at the second plane 575 in the wooden tie 505. The graph 565 shows the changes in density in different portions of the target, i.e. the wooden tie 505.

Figure 16:
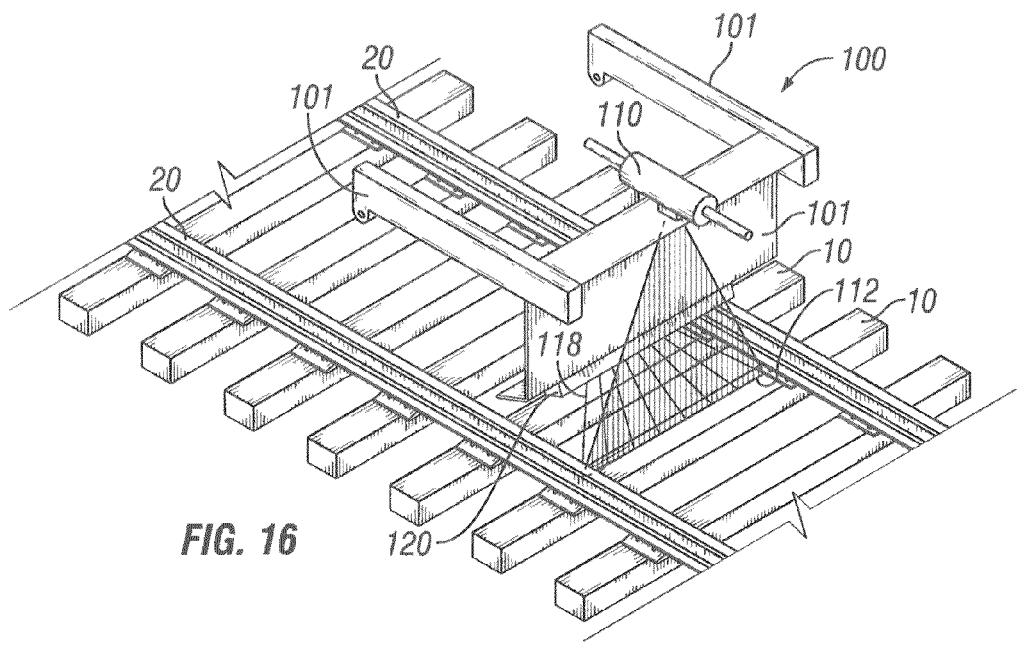
FIG. 16 shows an embodiment of an internal inspection system using a fan beam to detect the density of a target.

FIG. 16 shows one embodiment of an internal inspection system 100 that detects backscatter x-rays 118 from a target to determine the density of the target. The detection of backscatter x-rays 118 may permit the location of low density areas in a target as well as identifying the volume, size, and/or number of low density areas. Ties 10 are shown as a target in FIG. 16 for illustrative purposes. The internal inspection system 100 may be used to determine a change in density in various targets and not just ties 10 as would be appreciated by one or ordinary skill in the art having the benefit of this disclosure. The inspection system 100 includes an x-ray source 110 and a backscatter detector 120 connected to a frame 101. The frame 101 may be used to connect the inspection system 100 to various structures such as a vehicle or a static structure. The x-ray source 110 emits a fan beam 112 that irradiates the target and the backscatter detector 120 detects the backscatter x-rays 118 from the target. A change in the amount of backscatter x-rays detected by the detector 120 in comparison to a different portion of the target indicates that there may be a change in density within the target. Likewise, the amount of backscatter x-rays 118 detected from a single target may be compared to other identical targets to determine if the present target has an unexpected density. The internal inspection system 100 may flag the current target for additional inspection or notify an inspector that the detector 120 detected an abnormal level of backscatter x-rays 118 for a target. The abnormal level may be less or more backscatter x-rays 118 than expected.

Figure 17:
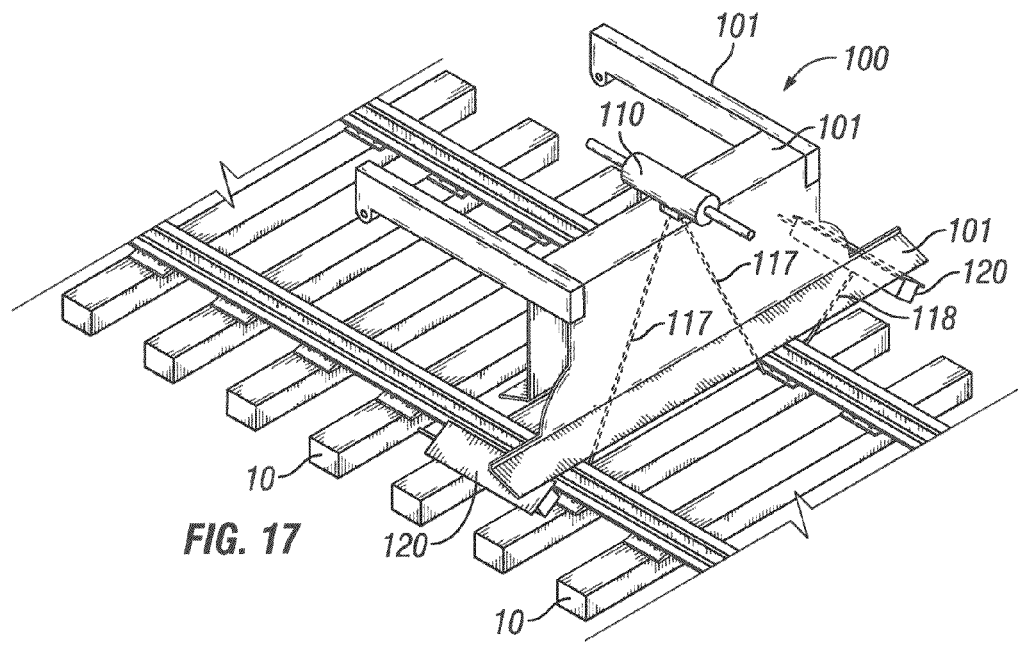
FIG. 17 shows an embodiment of an internal inspection system using a pencil beam to detect the density of a target.

FIG. 17 shows one embodiment of an internal inspection system 100 that detects backscatter x-rays 118 from a target to determine the density of the target using a pencil beam 117. Ties 10 are shown as a target in FIG. 17 for illustrative purposes. The internal inspection system 100 may be used to determine a change in density in various targets and not just ties 10 as would be appreciated by one or ordinary skill in the art having the benefit of this disclosure. The inspection system 100 includes an x-ray source 110 and two backscatter detectors 120 connected to a frame 101. The frame 101 may be used to connect the inspection system 100 to various structures such as a vehicle or a static structure. The detectors 120 may be positioned outside of the rails 20. The x-ray source 110 emits pencil beams 117 that irradiates the target and the backscatter detector 120 detects the backscatter x-rays 118 from the target. The pencil beams 117 may be located to determine whether a tie 10 has a change in density for the portion location underneath a rail 20.

A change in the amount of backscatter x-rays detected by the detectors 120 in comparison to a different portion of the target indicates that there may be a change in density within the target. Likewise, the amount of backscatter x-rays 118 detected from a single target may be compared to other identical targets to determine if the present target has an unexpected density. The internal inspection system 100 may flag the current target for additional inspection or notify an inspector that the detectors 120 detected an abnormal level of backscatter x-rays 118 for a target. The abnormal level may be less or more backscatter x-rays 118 than expected. The use of two pencil beams 117 and two detectors 120 location at opposite ends of a target may provide a notification of which portion of the target needs further inspection to determine a potential density change, such as a void, within the target.

Figure 18:
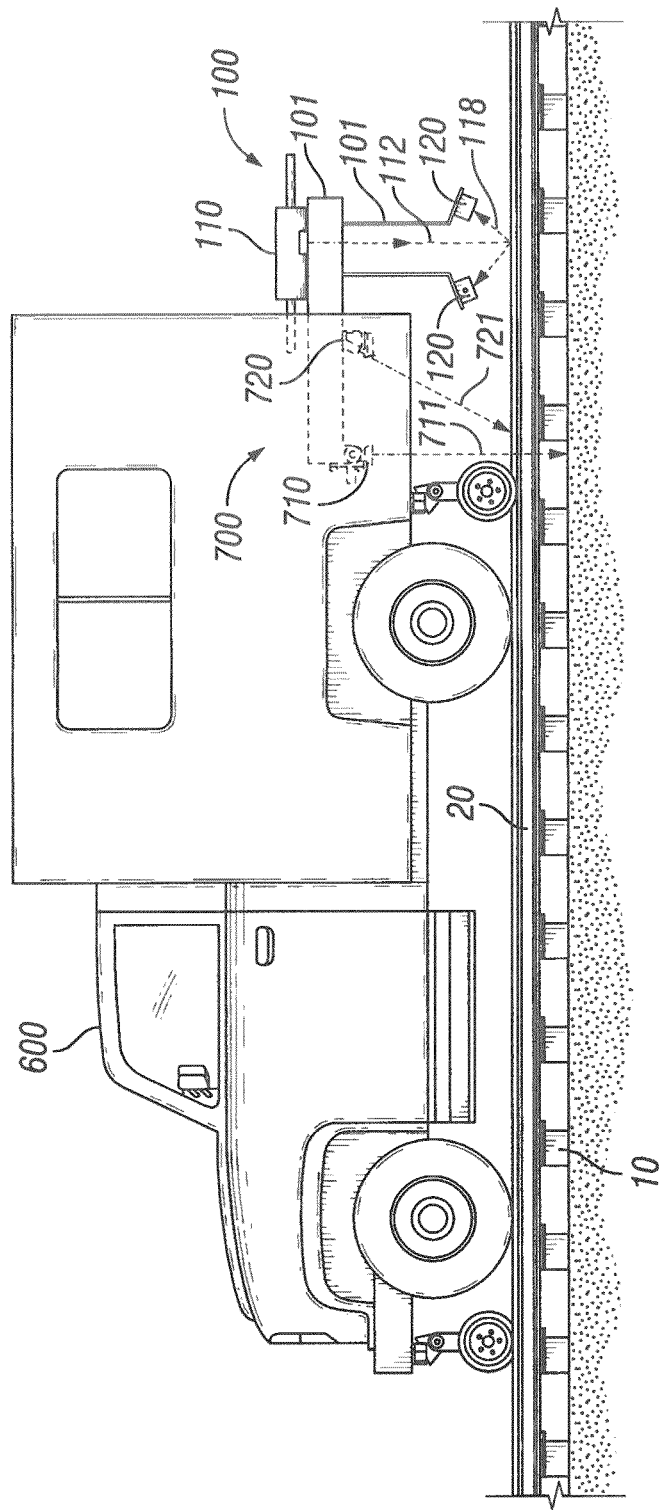
FIG. 18 shows an embodiment of an internal inspection system used with a surface scanning system.

FIG. 18 shows an internal inspection system 100 used in conjunction with a surface scan system 700. Both the internal inspection system 100 and the surface scan system 700 may be connected to a frame 101. The surface scan system 700 may be the Aurora system referenced above. The frame may be used to connect the systems to a vehicle 600 adapted to travel along the rails 20 of a railway. The internal inspection system 100 may include a source of x-rays 110 positioned to emit collimated x-rays in the form of a fan beam 112 between a two detectors 120. The detectors 120 are adapted to detect backscatter x-rays 118 from a target, such as railway components, and generate data based on the detection of backscatter x-rays 118 as discussed herein.

The surface scan system 700 may include a plurality of laser sources 710 that illuminate a portion of the railway including railway components with a laser 711. For example, the laser may illuminate one rail 20 and a portion of a tie 10 as the vehicle 600 travels down the rails 20 of a railway. The surface scan system 700 may include a plurality of optical devices 720, such as cameras, to capture images of the components and/or portions of the railway illuminated by the lasers 711. The field of view 721 of the optical devices may be directed to capture desired portions of the railway. As discussed above, images from the internal imaging system 100 may be compared to images from the surface scan system 700. Further, images from the surface scan system 700 may be used in conjunction with data, which may not necessarily be images, provided from the detectors 120 of the internal inspection system 100. For example, the internal inspection system 100 may provide data concerning the density of a target that is correlated with image and location information provided by the surface scan system 700.

Although this invention has been described in terms of certain preferred embodiments, other embodiments that are apparent to those of ordinary skill in the art, including embodiments that do not provide all of the features and advantages set forth herein, are also within the scope of this invention. Accordingly, the scope of the present invention is defined only by reference to the appended claims and equivalents thereof

TABLE OF REFERENCE NUMERALS FOR FIGS. 1-15

5 void in railroad tie
10 railroad tie
11 tie plate
12 spike
13 spike holes
15 crack in railroad tie
20 railway rail
25 rail base corrosion (RBC)
30 foreign object
50 manufacturing facility
100 internal inspection system
101 frame
110 collimated x-ray source
111 collimated x-rays
112 fan beam
113 aperture in x-ray source
114 collimation slot in x-ray source
115 backscatter x-rays from below collimation plane
116 backscatter x-rays from above collimation plane
117 pencil beam
118 backscatter x-rays from target
120 backscatter x-ray detector
125 collimation fins
130 target
135 collimation plane
140 CPU
150 display/monitor
170 forward bank of backscatter x-ray detectors
180 rear bank of backscatter x-ray detectors
190 backscatter x-rays
200 internal inspection system
205 rail of railway
210 ties of railway
211 x-ray fan beam
220-226 segmented backscatter x-ray detectors
230-236 segmented backscatter x-ray detectors
250 direction of travel of internal inspection system
300 x-ray source
305 emitted x-rays
310 target
315 backscatter x-rays
320 backscatter x-ray detectors
330 transmission x-ray detector
420 segmented backscatter x-ray detector
425 collimation fins
426 fastener
500 picture of wooden tie
505 wooden tie
515 break in wooden tie
525 break in wooden tie
520 spike hole in wooden tie
530 tungsten block in wooden tie
535 break in wooden tie 550 gray scale image of wooden tie
560 graph of data from segmented detector at first plane in tie
565 graph of data from segmented detector at second plane in tie
570 first plane in wooden tie
575 second plane in wooden tie
600 vehicle
700 surface scan system
710 laser source
711 laser
720 optical device/camera
721 field of view of optical device

What is claimed is:

1. A internal imaging system to inspect a plurality of targets along a predetermined path, the system comprising:
a vehicle configured to travel along the predetermined path;
a first x-ray source connected to the vehicle, the first x-ray source configured to irradiate the plurality of targets with a fan beam of x-rays;
a first detector connected to the vehicle, the first detector configured to detect backscatter x-rays from the plurality of targets.

2. The system of claim 1, wherein the predetermined path is a railway track.

3. The system of claim 2, wherein the plurality of targets comprises railway track components.

4. The system of claim 3, further comprising
a second x-ray source connected to the vehicle, wherein the first x-ray source is configured to irradiate at least a first rail of the railway track with the fan beam of x-rays and the second x-ray source is configured to irradiate at least a second rail of the railway track with a fan beam of x-rays; and
a second detector connected to the vehicle, the second detector configured to detect backscatter x-rays from the plurality of targets.

5. The system of claim 4, wherein first and second x-ray sources are positioned to irradiate the plurality of targets with fan beams between the first and second detectors.

6. The system of claim 3, wherein the first detector is a segmented detector.

7. The system of claim 6, wherein the first detector further comprises a collimation slot.

8. The system of claim 3, further comprising a processor in communication with the first detector.

9. The system of claim 8, wherein the processor is configured to determine a density of the plurality of targets from the reception of backscatter x-rays by the first detector.

10. The system of claim 8, wherein the processor is configured to generate internal images of the plurality targets from the reception of backscatter x-rays by the first detector.

11. The system of claim 10, further comprising a monitor to display the internal images of the plurality of targets.

12. The system of claim 8, further comprising a surface scanning system connected to the vehicle.

13. The system of claim 12, wherein the surface scanning system comprises at least one light source and at least one optical device, wherein the at least one light source illuminates a portion of the plurality of targets and the at least one optical device captures images of the illuminated portion of the plurality of targets.

14. A method of using an internal inspection system along a predetermined path to conduct an internal inspection of a plurality of targets, the method comprising:
moving the internal inspection system along a predetermined path, the inspection system comprising at least one source of x-rays and at least one first detector configured to detect backscatter x-rays;
irradiating the plurality of targets along the predetermined path with x-rays from the at least one source of x-rays;
detecting a portion of backscatter x-rays from the plurality of targets with the at least one first detector; and
generating data relating to an internal structure of the plurality of targets based on the detection of backscatter x-rays by the at least one first detector.

15. The method of claim 14, wherein the predetermined path is a railway track and the plurality of targets are railway track components.

16. The method of claim 15, further comprising detecting an object in at least one target of the plurality of targets, the object selected from the group consisting of a void, a foreign object, a material flaw, and a fastener.

17. The method of claim 15, further comprising analyzing the generated data to determine a density of at least a portion of at least one target of the plurality of targets.

18. The method of claim 15, wherein the data is an image of an internal structure of at least one target of the plurality of targets.

19. The method of claim 18, further comprising scanning the plurality of targets with a surface scan system, generating a surface image of at least one target of the plurality of targets from the surface scan, and comparing the surface image and the internal image of the at least one target.

20. The method of claim 14, wherein irradiating the plurality of targets further comprising irradiating the plurality of targets with a fan beam or a pencil beam of x-rays.

21. The method of claim 14, wherein irradiating the plurality of targets further comprising irradiating the plurality of targets with collimated x-rays.

22. The method of claim 14, further comprising positioning the at least one first detector in front of the at least one source of x-rays and positioning at least one second detector behind the source of x-rays.

23. The method of claim 22, wherein the at least one first detector is a first plurality of segmented detectors and the at least one second detector is a second plurality of segmented detectors.

24. The method of claim 14, further comprising analyzing the generated data to identify at least one internal feature of at least one target of the plurality of targets.

25. An inspection system, the system comprising:
a vehicle;
a source of collimated x-rays connected to the vehicle, the source of collimated x-rays configured to irradiate a plurality of targets positioned along a predetermined path of travel of the vehicle; and
a detector connected to the vehicle positioned to detect backscatter x-rays from the plurality of targets irradiated from the source of collimated x-rays, the detector configured to generate data upon detection of backscatter x-rays.

26. The system of claim 25, wherein the source of collimated x-rays emits a pencil beam or fan beam of x-rays.

27. The system of claim 25, further comprising a processor configured to determine a density or a cross-section of at least one of the plurality of targets based on the data from the detector.

28. The system of claim 25, further comprising a surface scan system connected to the vehicle, the surface scan system configured to generate images of at least a portion of the plurality of targets.

29. The system of claim 28, wherein the surface scan system comprises at least one light source and at least one optical device, wherein the at least one light source illuminates at least a portion of the plurality of targets and the at least one optical device captures images of the illuminated portion of the plurality of targets.

30. The system of claim 28, further comprising a processor configured to correlate the data from the detector with the image from the surface scan system.

31. The system of claim 28, further comprising a processor configured to process the data from the detector to generate internal images of at least a portion of the plurality of targets and to compare the internal images and the images from the surface scan system.

32. The system of claim 31 further comprising a monitor connected to the processor to display the internal images and the captured images.

* * * * *